(12) United States Patent
Manzke

(10) Patent No.: US 12,129,458 B2
(45) Date of Patent: Oct. 29, 2024

(54) FILTER SYSTEM FOR BIOPHARMACEUTICAL PROCESSES

(71) Applicant: Sartorius Stedim Biotech GmbH, Goettingen (DE)

(72) Inventor: Christian Manzke, Bovenden (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 0 days.

(21) Appl. No.: 17/126,482

(22) Filed: Dec. 18, 2020

(65) Prior Publication Data

US 2021/0102154 A1 Apr. 8, 2021

Related U.S. Application Data

(63) Continuation of application No. PCT/EP2019/060872, filed on Apr. 29, 2019.

(30) Foreign Application Priority Data

Jun. 19, 2018 (DE) ............... 10 2018 004 890.0

(51) Int. Cl.
  *B01D 63/08* (2006.01)
  *B01D 65/02* (2006.01)
  (Continued)

(52) U.S. Cl.
  CPC ........... *C12M 29/04* (2013.01); *B01D 63/081* (2013.01); *B01D 63/082* (2013.01);
  (Continued)

(58) Field of Classification Search
  CPC ...... C12M 29/04; C12M 23/40; C12M 41/00; B01D 63/081; B01D 63/084;
  (Continued)

(56) References Cited

U.S. PATENT DOCUMENTS

| 4,261,834 A | 4/1981 | deWinter |
| 4,849,102 A | 7/1989 | Latour et al. |
| (Continued) | | |

FOREIGN PATENT DOCUMENTS

| EP | 0818228 A1 | 1/1998 |
| JP | S555684 A | 1/1980 |
| (Continued) | | |

OTHER PUBLICATIONS

International Search Report, PCT/EP2019/060872, Jul. 16, 2019, 2 pages.
(Continued)

*Primary Examiner* — Pranav N Patel
(74) *Attorney, Agent, or Firm* — Edell, Shapiro & Finnan, LLC

(57) ABSTRACT

A filter system (100) for biopharmaceutical processes includes: at least one filter unit (10); and at least one distributor plate (200), against which the filter unit rests. A tubeless distributor unit (202) is arranged within the distributor plate and is fluidically connected to the filter unit. The distributor unit guides the fluid to be filtered to the filter unit and/or receives and discharges the filtered fluid from the filter unit. The distributor unit includes at least one active control element (232; 238), with which a fluid flow (14) through the distributor unit) and the filter unit is controlled in an open loop flow or a closed loop flow. The fluid connection between the filter unit and the distributor plate is tubeless. Also provided are a distributor plate (200) for a filter system (100) for biopharmaceutical processes and a method for producing a filter system (100) for biopharmaceutical processes.

19 Claims, 6 Drawing Sheets

(51) Int. Cl.
  *C12M 1/00* (2006.01)
  *C12M 1/34* (2006.01)
(52) U.S. Cl.
  CPC ......... *B01D 63/084* (2013.01); *B01D 65/022* (2013.01); *C12M 23/40* (2013.01); *C12M 41/00* (2013.01); *B01D 2313/105* (2013.01); *B01D 2313/18* (2013.01); *B01D 2313/243* (2013.01); *B01D 2321/346* (2013.01)
(58) Field of Classification Search
  CPC ............ B01D 65/022; B01D 2313/105; B01D 2313/18; B01D 2313/243; B01D 2321/346; B01D 61/145; B01D 61/147; B01D 63/082; B01D 2313/54; B01D 61/18; B01D 61/142; B01D 61/20; B01D 61/22
  See application file for complete search history.

(56) References Cited

U.S. PATENT DOCUMENTS

| | | | |
|---|---|---|---|
| 5,194,149 A | 3/1993 | Selbie et al. | |
| 5,599,447 A | 2/1997 | Pearl et al. | |
| 6,068,770 A * | 5/2000 | Niermeyer | B01D 61/20 210/450 |
| 6,139,741 A | 10/2000 | McGibbon | |
| 2003/0066794 A1 | 4/2003 | Diel | |
| 2004/0188331 A1 * | 9/2004 | Moscaritolo | B01D 35/143 210/90 |
| 2007/0056894 A1 * | 3/2007 | Connors | B01D 63/082 210/321.75 |
| 2008/0135500 A1 * | 6/2008 | Gagnon | B01D 63/082 210/321.72 |
| 2009/0294709 A1 * | 12/2009 | Stretch | F15B 13/0832 251/12 |
| 2010/0140153 A1 | 6/2010 | Telepciak et al. | |
| 2011/0111504 A1 | 5/2011 | Knebel et al. | |
| 2012/0174996 A1 * | 7/2012 | Cirou | B01D 61/20 137/544 |
| 2013/0118971 A1 * | 5/2013 | Sayer | B01D 65/00 210/321.75 |
| 2016/0059159 A1 * | 3/2016 | Steen | B01D 29/603 210/788 |

FOREIGN PATENT DOCUMENTS

| | | |
|---|---|---|
| JP | H1071326 A | 3/1998 |
| JP | 2000513656 A | 10/2000 |
| JP | 2003519004 A | 6/2003 |
| JP | 2011005478 A | 1/2011 |
| WO | 9857725 A1 | 12/1998 |
| WO | 2012105835 A1 | 8/2012 |

OTHER PUBLICATIONS

Korean Office Action with English translation, Application No. 10-2021-7001675, Issue date Jul. 14, 2022, 16 pages.

* cited by examiner

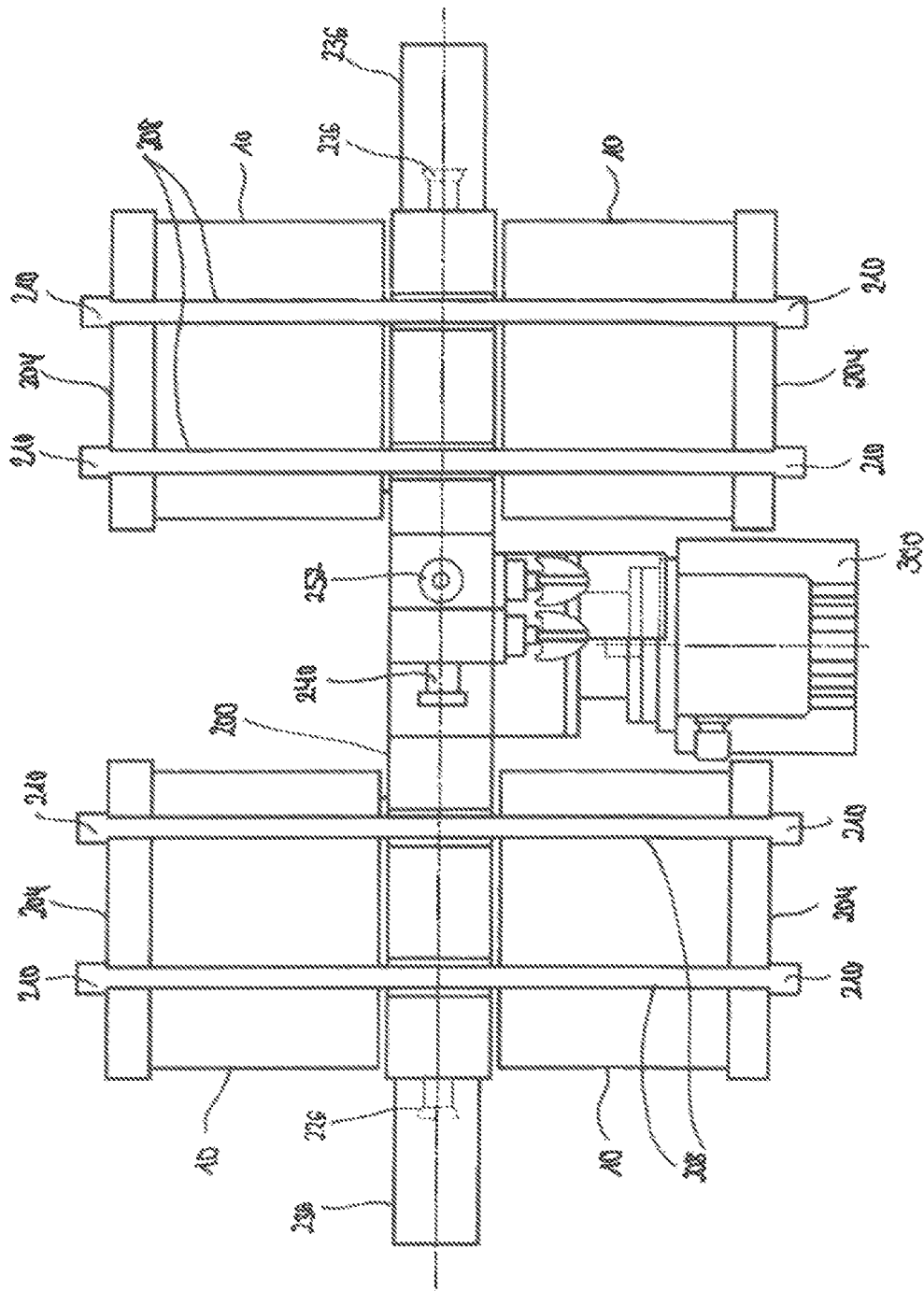

FILTER SYSTEM FOR BIOPHARMACEUTICAL PROCESSES

CROSS REFERENCE TO RELATED APPLICATIONS

This is a Continuation of International Application PCT/EP2019/060872 which has an international filing date of Apr. 29, 2019, and the disclosure of which is incorporated in its entirety into the present Continuation by reference. This Continuation also claims foreign priority under 35 U.S.C. § 119(a)-(d) to and also incorporates by reference, in its entirety, German Patent Application DE 10 2018 004 890.0 filed on Jun. 19, 2018.

FIELD OF THE INVENTION

The present invention relates to a filter system for biopharmaceutical processes, a distributor plate for biopharmaceutical processes, and a method for producing a filter system for biopharmaceutical processes.

BACKGROUND

Processes, such as, for example, cell separation (for example, by depth filtration), sterile filtration, chromatography steps, viral inactivation, virus filtration and/or crossflow filtration, are known from the biopharmaceutical industry. All of these processes constitute basic operations that can be carried out within a filter unit. Moreover, it is also known to connect a plurality of filter units to one another. Then the fluid to be filtered flows at least partially and, as a function of the selected processes, successively through the individual, interconnected filter units.

In order to guide the fluid to be filtered to a filter unit and also to discharge the fluid from said filter, hoses are used that permit both a sterile and non-sterile transfer. In particular, the supply hose, through which the fluid to be filtered can flow to the filter unit, can be connected to a pump that pumps the fluid to be filtered through the filter unit. In addition, other elements, such as, for example, sensors and valves, have to be integrated in the hoses, in order to regulate the supply of the fluid to and/or the discharge of the fluid out of the filter unit or to monitor the fluid flow or, more specifically, the fluid.

In this case the use of hoses leads to technical challenges, since various processes (such as, for example, crossflow filtration or virus filtration applications) can run under high pressure (up to 6 bar); and, hence, it is necessary to ensure a level of process safety that minimizes the risk of the hoses bursting or being torn off.

Furthermore, the process of connecting the various hoses to the filter unit is complicated, time consuming and susceptible to faults. In particular, it has to be ensured that the hose connection is sterile with respect to sterile apparatuses. In addition, after the hose connection has been connected, the filter system cannot be used immediately, since the entire system has to be first rinsed and sterilized.

SUMMARY

Therefore, one object of the present invention is to simplify the handling of a filter system and to permit rapid use of the filter system. In particular, the filter system has to ensure a high degree of process safety, so that both the operator and the product are protected.

According to one formulation, this object is achieved by a filter system for biopharmaceutical processes, said filter system comprising:
- at least one filter unit; and
- at least one distributor plate, against which the at least one filter unit rests and which comprises a distributor unit, which is arranged within the distributor plate and is fluidically connected to the at least one filter unit;
- wherein the distributor unit is configured to guide the fluid to be filtered to the at least one filter unit and/or to receive and discharge the filtered fluid from the at least one filter unit, and
- wherein the distributor unit comprises at least one active control element, with which a fluid flow, which flows through the distributor unit and the at least one filter unit, can be controlled in an open loop or closed loop manner,
- wherein the distributor unit is tubeless, and
- wherein the fluid connection between the at least one filter unit and the distributor plate is tubeless.

The term "filter unit" is to be understood, in particular, as meaning a unit, within which a special process step for the desired process is carried out. In particular, a separation of components of a fluid flow takes place within a filter unit. For example, a filter unit can be a unit for cell separation (for example, by depth filtration), for sterile filtration, for a chromatography step, for virus depletion or for crossflow filtration. In this case as well as in the prior art the filter unit can be selected as a standard filter unit with the desired specifications. If the filter system comprises a plurality of filter units, then these filter units can be identical or have properties that are at least partially different from one another. Different filter units, which, for example, use different separating media or are responsible for different processing steps of a method, can be connected to one another. Then it is possible to use the identical filter units, when a capacity expansion is desired. The connection between the filter units is preferably a parallel connection of the filter units, if the filter units are identical filter units. A serial connection is preferred if, for example, different filter units, which carry out different processing steps, are connected to one another.

The "filter system" can be used over and over again, but it is particularly suitable for just a single use, so that after the filter system has been used, it can be disposed of. As a result of the small number of parts of the filter system of the present invention, the filter system can be produced cost-effectively and, therefore, can be used as a disposable system.

The filter system can be sent to the user as an already assembled or, more specifically, preconfigured and/or sterile system, so that the user need only connect the filter system to the user's existing system (for example, to a container, in which the fluid to be filtered is contained, and/or actuators, such as, for example, a pump drive). In this case, it is, in particular, no longer necessary for the user to carry out rinsing operations or a sterilization process on the filter system (which is, for example, necessary for crossflow membranes). These steps can already be done at the factory before delivery of the filter system. Hence, the filter system simplifies the handling for the user and thereby saves the user time.

As a result of the direct tubeless connection between the distributor plate and the filter unit, it is possible to dispense with any and all hoses or, more specifically, flexible connections between these two elements. In addition, the distributor unit is integrated in the distributor plate, so that the distributor plate also eliminates the need for any hoses or, more specifically, flexible connections. By dispensing with these hose connections it is also possible to dispense with critical points, at which there is a risk for the integrity and/or sterility of the system. In particular, since the system can be delivered as an already assembled and sterile system, it is possible to eliminate the risk that the user makes errors in the assembly and thereby imperils the assurance that the filter system is closed and/or sterile.

By dispensing with the hoses, it is also possible, in particular, to avoid the need of having to constantly ensure or, more specifically, monitor the pressure resistance of the hoses. Furthermore, it is no longer necessary to provide measuring points in the hoses that could ordinarily be integrated only in sections in which the hose has a appropriate diameter.

In addition, the distributor unit has at least one active control element, with which the fluid flow through the distributor unit and through the at least one filter unit can be controlled in an open loop or closed loop manner. This aspect also offers the advantage that the necessary components for operating the filter system are preassembled, so that here, too, the handling for the user is improved.

The distributor unit comprises preferably a conduit system, which extends within the distributor plate and is configured to guide the fluid to be filtered and/or the filtered fluid.

The fluid to be filtered can be fed to the at least one filter unit through the conduit system; and the filtered fluid ("filtrate") can be discharged from the filter unit.

In other words, the conduit system has preferably at least one supply input or, more specifically, feed input or rather input port, through which the fluid to be filtered enters the conduit system and is subsequently fed to the at least one filter unit. Furthermore, the conduit system has preferably at least one discharge output or, more specifically, output port, through which the filtered fluid can be discharged out of the distributor plate. Therefore, before the filter system is put into operation, the user has to connect a tank with the fluid to be filtered to the ports in a suitable manner and has to connect a collecting container with the filtered fluid to the distributor plate. The ports are preferably sterile connectors.

Since the conduit system is integrated in the distributor plate or, more specifically, incorporated in the distributor plate, there are no contact points within this conduit system between individual hose elements that could jeopardize the sterility of the filter system. Any and all hoses for guiding the fluid flow can be dispensed with.

Furthermore, it is preferred that the active control element comprise at least one pump head that can be connected to a pump drive, in order to pump the fluid through the distributor plate and the at least one filter unit.

In other words, the relatively inexpensive pump head can be integrated or, more specifically, incorporated in the distributor plate. Before the filter system is put into operation, the pump head itself can then be connected to a pump drive of the user in a simple way. This can be done, for example, by simply plugging the pump head onto the pump drive. Such a configuration also allows, in particular, a single use of the filter system.

The pump is used to press the fluid to be filtered through the at least one filter unit at a corresponding pressure. In this case the pressure to be applied to the fluid flow depends, in particular, on the filter unit that is used. As a result of the aforementioned method of connecting the pump drive to the distributor plate, the pump drive can be connected to the filter system in a simple way and without any hoses. At the same time the handling for the user is significantly improved.

Since the pump drive is normally not sterilizable, the pump drive can be separated from the fluid by a membrane or, more specifically, a septum or a corresponding mechanical coupling. The membrane or mechanical coupling itself can be integrated in the distributor plate and can already be sterilized at the factory as part of the filter system.

The active control element comprises preferably at least one valve that is configured to control in an open loop or closed manner the fluid flow through the distributor plate and/or the at least one filter unit.

The at least one valve is integrated preferably in the conduit system. In this case the at least one valve can be configured to control in an open loop or closed loop manner the fluid flow through the distributor plate. The at least one valve can build up the necessary dynamic pressure, in order to press the fluid through the filter membrane with the required pressure. Furthermore, the valve can be used, for example, to allow the fluid flow to flow only in one direction of the conduit system, and/or to control in an open loop or closed loop manner the flow rate through the conduit system. Furthermore, a valve can be arranged at a feed input on the distributor plate, in order to control in an open loop or closed loop manner the inflow into the distributor plate.

The valve can be operated manually, pneumatically or electrically. In particular, the valve can be connected to a control apparatus of the user, in order to control the valve with the control apparatus.

Furthermore, it is preferred that the distributor unit comprise at least one sensor that is configured to measure at least one parameter of the fluid flow within the distributor unit.

The sensor is preferably a pressure sensor that is integrated in the distributor plate. In this case the pressure sensor can be arranged in such a way that the pressure sensor measures or, more specifically, monitors the pressure of the fluid flow within the conduit system of the distributor plate. In this way it can be ensured that the fluid to be filtered impinges on the filter unit with the required pressure. For this purpose the pressure sensor can be connected to the control apparatus of the user. Then the pressure can be regulated either with the pump or the aforementioned valves using the measured values.

For example, the pressure, the volume flow, the UV value, the pH value, the turbidity and/or the viscosity of the fluid can be measured using the at least one sensor. Furthermore, it is also possible to measure the conductivity, the volumetric flow and/or the UV absorption.

Furthermore, the filter system comprises preferably at least one end plate, which is connected to the distributor plate through at least one retaining element, wherein the filter unit is arranged between the distributor plate and the end plate and is held on the distributor plate with the end plate.

In other words, the at least one filter unit can be clamped between the distributor plate and the end plate. The at least one retaining element serves as a connecting element between the distributor plate and the end plate and is configured to apply the necessary holding force for the at least one filter unit.

The retaining element is preferably a retaining rod that can be connected to the end plate and the distributor plate with a threaded joint.

The end plate is advantageous, in particular, for designs of a filter system, in which more than one filter unit is arranged on the distributor plate. The end plate can be used to apply the necessary retaining force, in order to hold the filter units on the distributor plate.

Furthermore, it is preferred that the distributor plate be made of plastic.

As a result of the distributor plate being made of plastic, the distributor plate can be produced cost effectively, so that the distributor plate is suitable for a single use. This can be done, for example, using an injection molding process, 3D printing or CNC milling process.

In a preferred embodiment the at least one filter unit and/or the distributor plate can be sterilized by gamma irradiation, gassing and/or autoclaving. In a particularly preferred embodiment the at least one filter unit and/or the distributor plate can be sterilized by gamma irradiation.

If the filter unit and the distributor plate can be sterilized using these methods, then the entire filter system can be sterilized as a unit and subsequently delivered to the user as a sterile product. The user no longer has any sterilization measures that need to be carried out before the system is used. For this purpose sterile connectors are used preferably as connecting elements on the distributor plate, where these connecting elements are used to feed the fluid to be filtered to the distributor plate and to discharge the filtered fluid from the distributor plate.

In this case gamma irradiation offers, for example, the advantage that sterilization of the filter system can be carried out in an inexpensive and simple way; and the filter system is not exposed to a high thermal load.

The filter system comprises preferably at least one first filter unit and at least one second filter unit, with the at least one first and the at least one second filter unit resting on opposite sides of the distributor plate.

By arranging the filter units on opposite sides of the distributor plate, the filter area to be used can be enlarged in a simple way.

The filter unit and the distributor plate are preferably adhesively bonded to one another or are injection molded from one piece.

In accordance with an additional aspect of the present invention, the present object is achieved with a distributor plate for a filter system for biopharmaceutical processes, said distributor plate comprising a distributor unit, which is arranged within the distributor plate and can be fluidically connected to at least one filter unit, in that the filter unit rests against the distributor plate;
  wherein the distributor unit is configured to guide the fluid to be filtered to the at least one filter unit and/or to receive and discharge the filtered fluid from the at least one filter unit, and
  wherein the distributor unit comprises at least one active control element, with which a fluid flow, which flows through the distributor unit and the at least one filter unit, can be controlled in an open loop or closed loop manner,
  wherein the distributor unit is tubeless, and
  wherein the fluid connection between the at least one filter unit and the distributor plate is tubeless.

In accordance with another aspect of the present invention, the present object is achieved with a method for producing a filter system for biopharmaceutical processes, said method comprising:
  providing at least one filter unit; and
  providing at least one distributor plate, which has a tubeless distributor unit, which is arranged within the distributor plate, and at least one active control element; and
  arranging tubelessly the at least one filter unit on the distributor plate in such a way that the at least one filter unit and the distributor unit are fluidically connected to one another;
  wherein the distributor unit is configured to guide the fluid to be filtered to the at least one filter unit and/or to receive and discharge the filtered fluid from the at least one filter unit, and
  wherein the at least one active control element is configured to control in an open loop or closed loop manner a fluid flow, which flows through the distributor unit and the at least one filter unit.

These and other objects, features and advantages of the present invention will become more apparent from a study of the following detailed description of preferred embodiments and the accompanying drawings. It should also be noted that although embodiments are described separately, individual features of these embodiments can be combined to form additional embodiments.

BRIEF DESCRIPTION OF THE DRAWINGS

FIG. 6 shows an additional embodiment of a filter system with four filter units.

DETAILED DESCRIPTION

Figure 1:
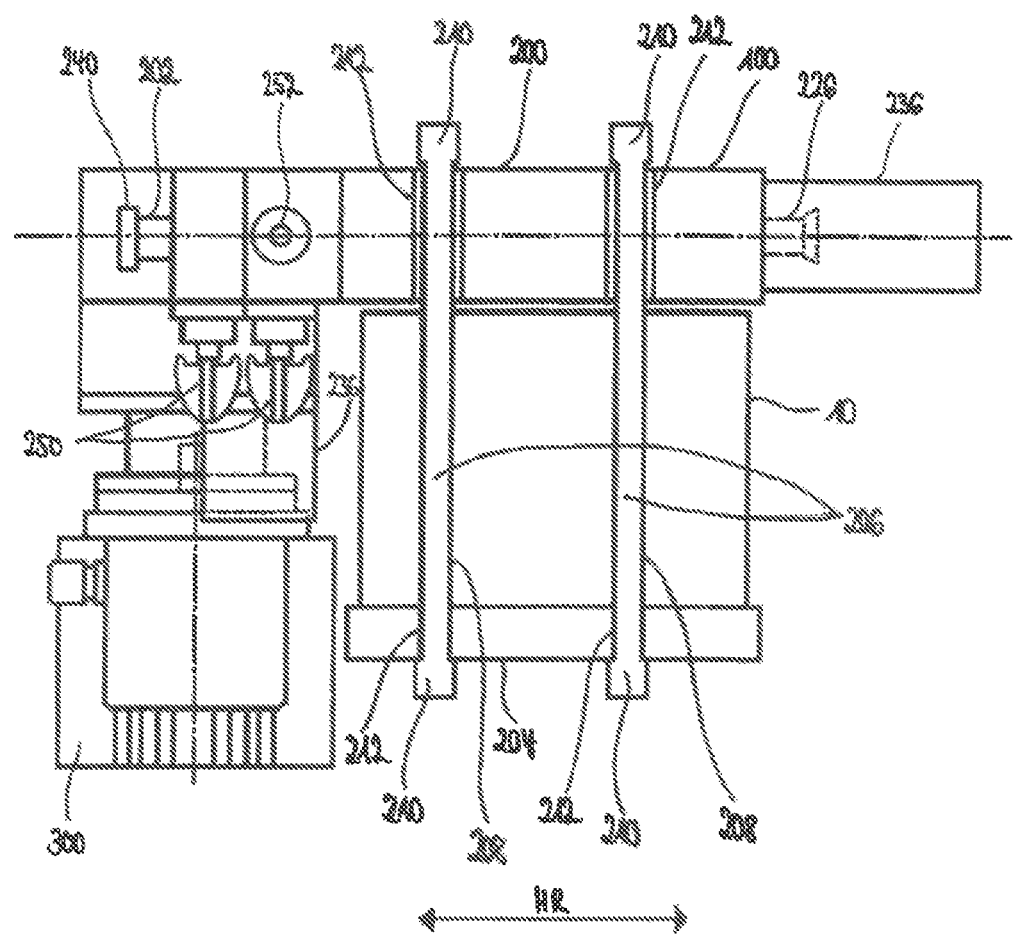
FIG. 1 a plan view of a filter system with a filter unit.

The filter system 100 of the present invention for biopharmaceutical processes comprises one or more filter units 10. The filter units 10 can be disposable filter units, which are designed for single use, or reusable filter units. FIG. 1 shows a plan view of the filter system 100 with one filter unit 10. However, a plurality of filter units 10 can also be connected in series or parallel to one another in the filter system 100. The filter system 100, described below, is configured, in particular, for crossflow filtration. However, the filter system 100 can also be used for other filtration methods. In this case the fluid guide in the distributor plate, described below, is adapted as a function of the filter units 10 or, more specifically, the types of filters that are used.

In addition to the at least one filter unit 10, already mentioned above, the filter system 100 comprises a distributor plate 200, against which the at least one filter unit 10 rests. The distributor plate 200 can be designed as a disposable distributor plate or as a reusable distributor plate. In particular, the distributor plate 200 can be made of plastic, as a result of which it is suitable in an advantageous way as a disposable element. The distributor plate 200 is preferably injection molded. In this case the at least one filter unit 10 is arranged on the distributor plate 200 in such a way that at least one filter medium (not shown here), which is located in the filter unit 10, extends substantially parallel to the distributor plate 200.

A distributor unit 202, which is configured to be in fluid communication with the at least one filter unit 10, is integrated in the distributor plate 200.

The distributor plate 200 can be adhesively bonded to the filter unit 10 (in the case of a plurality of interconnected filter units 10, the filter unit 10, which rests directly against the distributor plate 200) or can be injection molded together with the at least one filter unit 10. Furthermore, adjacent filter units 10 can also be adhesively bonded to one another or be injection molded together. As shown in FIG. 1, the at least one filter unit 10 can be held alternatively or additionally on the distributor plate 200 with at least one end plate 204 and at least one retaining element 206. In this case the at least one filter unit 10 is arranged between the distributor plate 200 and the end plate 204. The end plate 204 and the distributor plate 200 are connected to one another with the at least one retaining element 206. As shown in FIG. 1, the retaining element 206 can be embodied as a retaining rod 208 or, more specifically, may comprise at least one retaining rod 208. In FIG. 1, the end plate 204 and the distributor plate 200 are connected through four retaining rods 208. Only two of the retaining rods 208 are visible in FIG. 1 on account of the perspective view employed.

The retaining rods 208 can pass through the distributor plate 200 and the end plate 204 with the aid of through holes, with the ends of the retaining rods 208 projecting in each case beyond the distributor plate 200 and the end plate 204. At least one lock nut 210 is screwed onto each of these ends. This arrangement prevents the retaining rod 208 from slipping out and permits the necessary pressure to be adjusted to the at least one filter unit 10 based on the position of the lock nut on the retaining rod 208, in order to hold the at least one filter unit securely between the distributor plate 200 and the end plate 204.

As an alternative, as shown in FIG. 1, notches or, more specifically, recesses 212 may be formed in an upper side or lower side (not visible here) of the distributor plate 200 and the end plate 204, into which the retaining rods 208 are inserted, respectively. The retaining rods 208 are also secured here, as described above, with the lock nuts 210.

The end plate 204 and the retaining elements 206 can be made of plastic or metal.

Figure 2:
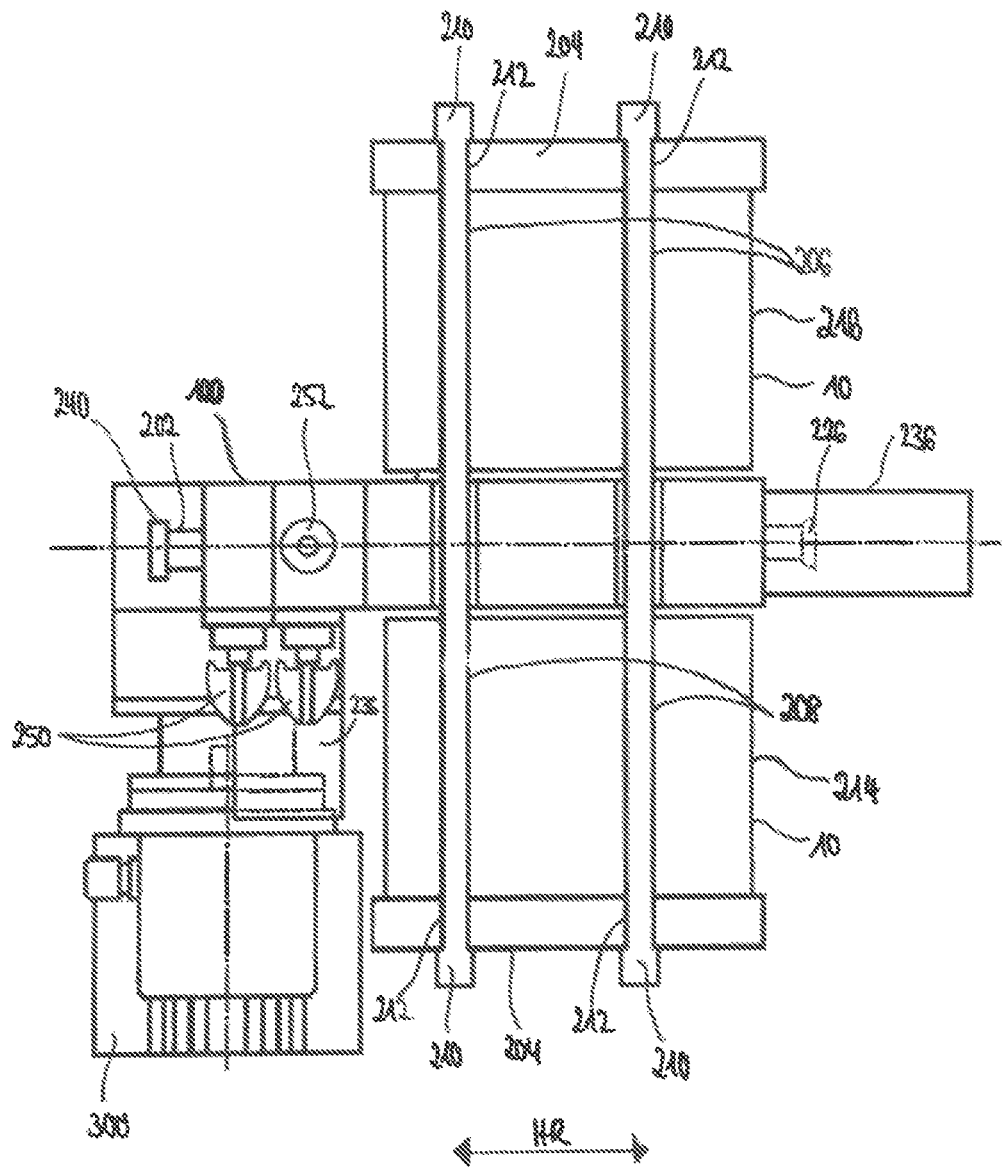
FIG. 2 a plan view of a filter system with two filter units, which are arranged on opposite sides of a distributor plate.

FIG. 2 shows a further embodiment of a filter system 100. The filter system 100 in FIG. 2 differs from the filter system 100 from FIG. 1, in that here at least one additional filter unit 10 rests against the distributor plate 200. Therefore, only the distinguishing features are described below. All other definitions and descriptions with respect to FIG. 1 also apply to FIG. 2.

As shown in FIG. 2, the filter system 100 in this embodiment comprises a first filter unit 214 and a second filter unit 216 resting against opposite sides of the distributor plate 200. Although in FIG. 2 individual filter units 10 are shown on the opposite sides of the distributor plate 200, a plurality of filter units 10 can also be arranged on each of the sides, with said filter units 10 being connected to one another in parallel or in series. This configuration is carried out as a function of the required filter area of the filter system 100.

The retaining rods 208, which are used, have preferably such a length that they are suitable for securing both the first filter unit 214 and the second filter unit 216 to the distributor plate 200, as shown in FIG. 2. However, it is also possible for each filter unit 10 to be separately secured by itself by corresponding retaining elements 206 or, more specifically, retaining rods 208.

Figure 3:
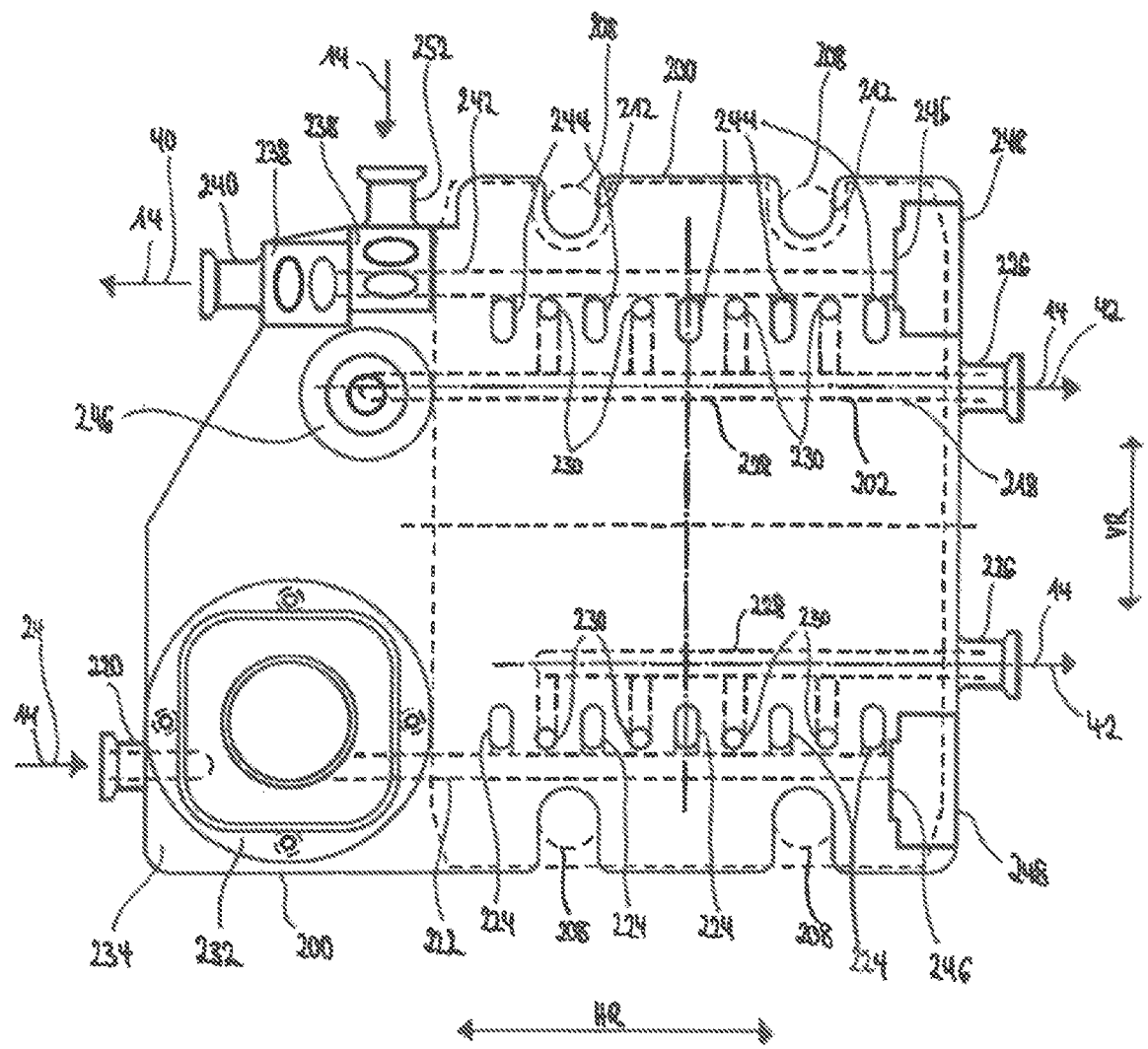
FIG. 3 shows a side view of the distributor plate.

FIG. 3 shows a side view of a distributor plate 200. The broken lines show a tubeless conduit system 218 that is integrated in the distributor plate 200 as part of the distributor unit 202. The conduit system 218 extends more or less within the distributor plate 200 or, more specifically, is incorporated in the distributor plate 200. As a result, any and all hoses can be dispensed with.

The medium to be filtered can be guided to the at least one filter unit 10 through the conduit system 218. After passing through the at least one filter unit 10, the separated fluid flows 14 can then be discharged again through the conduit system 218 in the distributor plate 200. Any and all hoses can be dispensed with not only within the distributor plate 200, but also for the fluid connection between the distributor plate 200 and the at least one filter unit 10, so that the distributor unit 202 and the at least one filter unit 10 are fluidically connected to one another without hoses.

The conduit system 218 comprises at least one input port 220, through which the filter system 100 can be fed a medium to be filtered. At this input port 220 the filter system 100 can be connected to at least one tank (not shown here), in which the medium to be filtered is stored. As shown in FIG. 3, the input port 220 can be a connecting piece. In particular, the input port 220 can be a sterile connector. The input port 220 is arranged on the left side of the distributor plate 200 in FIG. 3. The input port 220 is located preferably at a lower end of the distributor plate 200 with respect to a vertical direction VR.

The fluid flow 14 can flow into the distributor plate 200 through the input port 220 and then flow into a feed line 222. In this case the feed line 222 extends preferably in the horizontal direction HR and is connected to at least one inflow opening 224, through which the fluid to be filtered can flow into the at least one filter unit 10. As shown in FIG. 3, a plurality of inflow openings 224 can be arranged along the horizontal direction HR. Furthermore, inflow openings 224 can be arranged on a plurality of other planes (with respect to the vertical direction VR) of the distributor plate 200, so that the fluid to be filtered can flow into the filter unit 10 on a plurality of planes of the filter medium. The inflow openings 224 have preferably a slot shaped cross section with preferably rounded corners, but can also be round or oval, for example.

At least one permeate output port 226, which is used to discharge the permeate from the distributor plate 200, is formed preferably on the preferably opposite side of the distributor plate 200, on which the input port 220 is arranged. This output port as well as the input port 220 can be configured as a connecting piece. In particular, the permeate output port 226 can be embodied as a sterile connector. FIG. 3 shows two permeate output ports 226, which are arranged so as to be preferably offset in the vertical direction VR.

In each case, for example, a hose (not shown here), through which the permeate (i.e., that portion of the fluid flow 14 that has passed through the filter medium) can be discharged from the distributor plate 200, can be attached to the aforementioned permeate output ports 226. The permeate output ports 226 are connected in each case to a permeate discharge line 228, which extends preferably in the horizontal direction HR in the distributor plate 200. The permeate discharge line 228 is connected to at least one permeate discharge opening 230, through which the permeate from the at least one filter unit 10 can flow into the permeate discharge line 228. As shown in FIG. 3, a plurality of permeate discharge openings 230 can be arranged along the individual permeate discharge lines 228. In this embodiment the permeate discharge opening 230 itself has a circular cross section, but, as an alternative, can be oval or slot shaped. Inflow openings 224 and permeate discharge openings 230 can be located on one plane and can be arranged in an alternating manner.

Furthermore, the filter system 100 comprises at least one retentate output port 240, through which the retentate (i.e., that portion of the supplied fluid that has not passed through the filter medium in the filter unit 10) can be discharged out of the distributor plate 200. The retentate output port 240 can also be configured as a connecting piece and/or as a sterile connector. As shown in FIG. 3, the retentate output port 240 can be arranged on the same side of the distributor plate 200 as the input port 220. Preferably, the retentate output port 240 is arranged above the input port 220 with respect to the vertical direction VR or, more specifically, at an upper end of the distributor plate 200.

For example, a hose (not shown here), through which the retentate can be discharged out of the distributor plate 200, can be connected to the retentate output port 240. The retentate output port 240 is connected to a retentate discharge line 242, which extends preferably in the horizontal direction HR in the distributor plate 200. The retentate discharge line 242 is connected to at least one retentate discharge opening 244, through which the retentate from the at least one filter unit 10 can flow into the retentate discharge line 242. As shown in FIG. 3, a plurality of retentate discharge openings 244 can be arranged along the retentate discharge line 242. The retentate discharge opening 244 may be configured in a manner similar to the inflow opening 224. Retentate discharge openings 244 and permeate discharge openings 230 can be located on one plane and arranged in an alternating manner.

If in each case at least one filter unit 10 is arranged on opposite sides of the distributor plate 200, then at least one further inflow opening 224, at least one further permeate discharge opening 230 and at least one further retentate discharge opening 244 are arranged on a rear side (not shown) of the distributor plate 200 that correspondingly connects the feed line 222, the permeate discharge line 228 and the retentate discharge line 242 to the at least one additional filter unit 10 on the rear side of the distributor plate 200.

In order to ensure a fluid flow 14 through the filter system 100 and to generate the necessary pressure required to make the filtration process feasible, a pump (not shown in FIG. 3) is needed. This pump can be connected to the distributor plate 200. In order to provide a quick and easy connection option, a pump head 232 is integrated in the distributor plate 200 as an active control element and as part of the distributor unit 202. If the distributor plate 200 is made, for example, of plastic, then the pump head 232 can be incorporated in the distributor plate 200 as part of an injection molding process. Since the pump head 232 is an inexpensive component, the filter system 100 can, therefore, be used as a single use system, i.e., the filter system 100 can be disposed of after use. The pump drive 300 itself can be reused. The pump or, more specifically, pump head is arranged preferably in or rather on the distributor plate 200 in such a way that the pump is connected to the feed line 222. Furthermore, the pump head 232 can comprise a septum so that the pump does not come into contact with the fluid flow 14 in the distributor plate 200.

The pump drive 300 can be connected, for example, to the pump head 232 with a threaded coupling mechanism or with a snap lock. FIGS. 1 and 2 show a state, in which the pump drive 300 is already connected to the filter system 100 or, more specifically, is joined to the distributor plate 200.

In addition, the distributor unit 202 can contain at least one sensor, which is also integrated in the distributor plate 200. An integrated sensor is preferably a disposable sensor, when the filter system is used as a disposable system. As an alternative or in addition, at least one sensor 236 can be connected to the distributor plate 200 and, thus, can be reused. For this possibility the distributor plate 200 has preferably an integrated connecting point.

FIG. 3 shows an embodiment, in which a plurality of sensors 236 can be connected to the distributor plate 200. The connecting point can have preferably a septum 246. This aspect is shown in FIG. 3, for example, with respect to the upper permeate discharge line 228. In this case a connectable sensor 236 would be connectable in such a way that the fluid flow 14 in the upper permeate discharge line 228 can be measured. The connectable sensor 236 would be connectable in such a way that the sensor 236 itself would extend beyond the image plane (i.e., perpendicular to the horizontal direction HR).

Furthermore, the distributor plate 200 can have at least one connecting recess 248 that is used as a connecting point for a sensor 236. In this embodiment FIG. 3 shows on the right-hand side of the distributor plate 200 in each case one connecting recess 248, which allows each sensor 236 to be connected to the feed line 222 and the retentate discharge line 242. FIGS. 1 and 2 show a state, in which a sensor 236 is arranged on or rather in the connecting recess 248; or, more specifically, a sensor 236 is connected to the distributor plate 200.

In this case each of the aforementioned sensors 236 is arranged on or in the conduit system 218 of the distributor plate 200 so that the sensor 236 is in contact with the fluid flow 14 through the distributor plate 200. As a result, different parameters of the fluid can be monitored. The sensor 236 itself can be connected to a control apparatus for monitoring by the user, whereby this control apparatus is arranged outside the filter system 100.

The sensor 236 may be a pressure sensor 236 that monitors the pressure of the fluid flow 14. Should the pressure of the fluid flow 14 deviate from the intended values, then the pressure of the fluid flow 14 can be regulated, for example, with the aid of the pump, which can also be connected to the control apparatus.

Furthermore, at least one valve 238 can be integrated in the distributor plate 200 as an active control element and as part of the distributor unit 202. The valve 238 is arranged preferably in or on the conduit system 218. In particular, it is preferred that the valve 238 be arranged on or upstream of a retentate output port 240, as shown in FIG. 3. Primarily the valve 238 can ensure that the fluid flow 14 through the distributor plate 200 can only take place in one direction. In this way a reverse flow can be prevented. In addition, a further flow, an inflow or an outflow of the fluid flow 14 into or out of the distributor plate 200, respectively, can be blocked by a valve 238. As an alternative, the fluid flow 14 itself can also be controlled in an open loop or closed loop manner by the valve 238. For example, the pressure of the fluid flow 14 can be influenced as a function of the position or open position of the valve 238. For this purpose the valve 238 can be connected, for example, to the control apparatus. The valve 238 can be operated manually, pneumatically or electrically with the control apparatus. FIGS. 1 and 2 show valve adjusters 250, with which the valves 238 can be adjusted. These valve adjusters can be already preassembled or can be connected to the distributor plate 200.

In addition, the distributor plate 200 can have at least one feed port 252, through which an additional medium can be fed to the fluid flow 14 in the distributor plate 200. The feed port 252 can be configured as a connecting piece and/or as a sterile connector. In principle, the feed port 252 can be arranged at any desired position on the distributor plate 200, where the addition of a medium to the fluid stream 14 is desired. As shown in FIG. 3, the feed port 252 can be positioned in such a way that an addition of a medium to the retentate is possible. For this purpose the feed port 252 can be arranged on the upper side of the distributor plate 200 and can be connected to the retentate discharge line 242. The feed port 252 is arranged preferably upstream of the retentate output port 240 with respect to the direction of flow. As shown in FIG. 3, the feed port 252 can have a valve 238, as described above. At variance with the description above, it is also possible for the retentate output port 240 and the feed port 252 to be interchanged.

For example, a diafiltration medium and/or a buffer can be fed to the retentate through the feed port 252 in FIG. 3.

Figure 4:
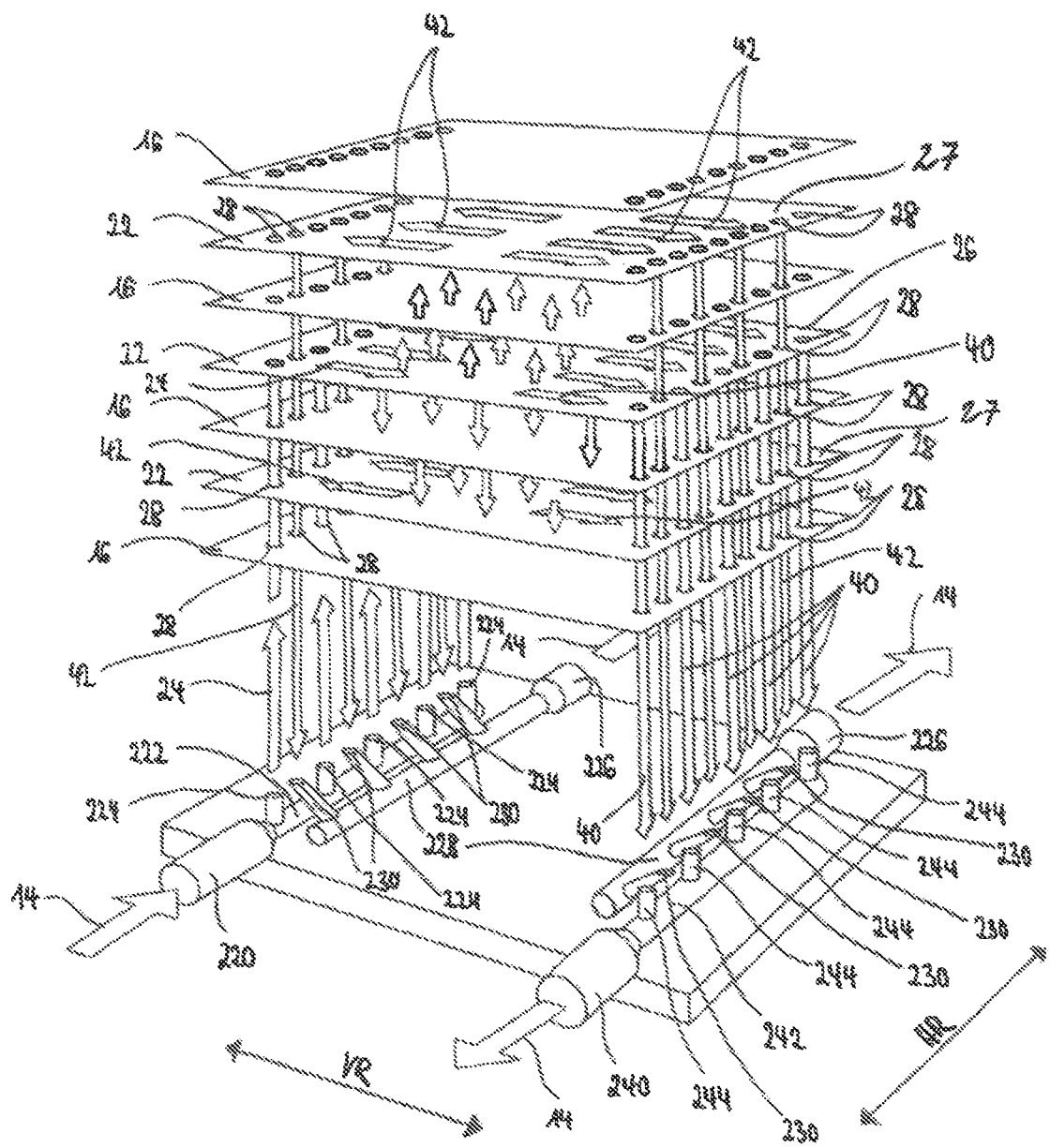
FIG. 4 shows an exploded view of a filter unit for crossflow filtration.

FIG. 4 shows by way of example a filter unit 10 for crossflow filtration that can be used in the filter system 100, described above. However, any other filter unit 10 can be used for the filter system 100, if the fluid stream 14 through the filter unit 10 is compatible with the distributor plate 200.

The exploded view in FIG. 4 shows in schematic form the feed lines and the discharge lines of the distributor plate 200 in the lowermost plane, where the filter unit 10 is fed and the retentate and permeate can be discharged through these feed lines and discharge lines, respectively. Therefore, any and all information about these lines that has already been given above with respect to the distributor plate 200 applies correspondingly to FIG. 4. In order to illustrate how the filter unit 10 is arranged on the distributor plate 200 in the assembled state, the horizontal direction HR and the vertical direction VR are shown in FIG. 4.

The filter unit 10 has preferably at least one filter medium 16 that comprises at least one porous material that is then selected or rather used as a function of the particles or, more specifically, substances that are to be filtered out of the fluid flow 14 with the aid of the filter unit 10. For example, the filter medium 16 may be a virus filter, a sterile filter, a depth filter or a membrane adsorber.

In FIG. 4, the filter unit 10 has a plurality of layers of a filter medium 16. These layers are stacked one on top of the other and are spaced apart from one another preferably by substantially permeable (in particular, net-like or fabric-like) spacers 22.

Both the filter media 16 and the spacers 22 have through holes 28 on opposite sides. These through holes are arranged along the horizontal direction HR. If the filter media 16 and the spacers 22 are stacked one on top of the other, the through holes 28, which overlap each other, form a channel. Each of these channels is configured to conduct a fluid flow 14. For this purpose the channels are connected in each case to either the feed line 222, one of the permeate discharge line 228 or the retentate discharge line 242.

Channels, which are in communication with the feed line 222, are configured to guide a feed flow 24. In this case the feed flow 24 comprises the medium to be filtered. The feed flow 24 is guided to a spacer 22, which is arranged between two filter media 16 and is referred to herein as the feed spacer 26. Then the feed flow 24 flows between an upper side of the feed spacer 26 and a filter medium 16 and a lower side of the feed spacer 26 and a filter medium 16.

The filter medium 16 is fluidically permeable, so that the filter medium-specific substances cannot pass through the filter medium 16. Filter medium-specific substances, which cannot pass through the filter medium 16, are transported away from the filter unit 10 as a retentate. However, that portion of the feed flow 24 that can pass through the filter medium 16 is transported away from the filter unit 10 as a permeate.

Since the feed flow 24 flows along the filter media 16, one portion of the feed flow 24 can pass through the filter medium 16. The other part of the feed flow 24, which cannot pass through the filter medium 16 (retentate discharge flow 40), continues to flow to the feed spacer 26 to the opposite side of the feed spacer 26, where it enters the respective channels that are configured to guide the retentate discharge flow 40 to a retentate feed line 242.

Then that portion of the feed flow 24 that can pass through a filter medium 16 flows to the opposite side of the filter medium 16, through which it has passed. This portion of the feed flow 24 is now referred to as a permeate discharge flow 42. This permeate discharge flow flows between the filter medium 16 and a spacer 22 to the opposite sides of the spacer 22 in channels that are configured to guide the permeate discharge flow 42 to the respective permeate discharge line 228. This spacer 22 is referred to herein as a permeate spacer 27.

The desired fluid guide, described above, in the respective channels or, more specifically fluid connections can be achieved, for example, by selectively sealing with sealing elements (for example, silicone rings) the corresponding openings of the through holes 28 to the intermediate spaces between the filter medium 16 and the spacer 22 (i.e., feed spacer 26 or permeate spacer 27).

In the assembled state of the filter system 100, the channels of the filter unit 10, which is arranged adjacent to the end plate 204, are closed, preferably fluidically, to the outside. For example, the channels can be adhesively bonded or closed by injection molding. As an alternative, a plastic plate, which is arranged between the end plate 204 and the filter unit 10, which is arranged adjacent to the end plate 204 and which is, for example, adhesively bonded to the filter unit 10, can close the channels. Closing the channels can prevent the end plate 204 from being contaminated by the fluid. In this way it can be ensured that the end plate 204 can be reused.

The filter system 100, described above, can be delivered as a unit to the user in an advantageous way, in order to be connected to the user's existing system. Preferably the filter system 100 is already preassembled and sterilized, so that the user only has to insert the filter system 100 into his system with just a few simple steps. The filter system 100 itself does not require any hoses, so that the use of the filter system 100 for the user is very simplified.

Figure 5A:
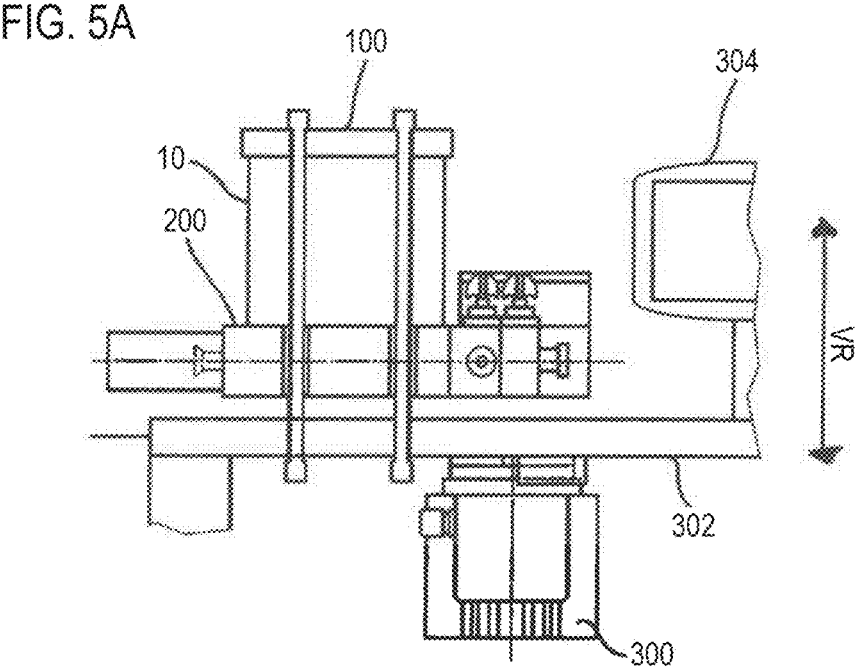
FIGS. 5A and 5B show different types of assembly of the filter system on a work bench, in particular in a vertical orientation (FIG. 5A) and in a horizontal orientation (FIG. 5B)
Figure 5B:
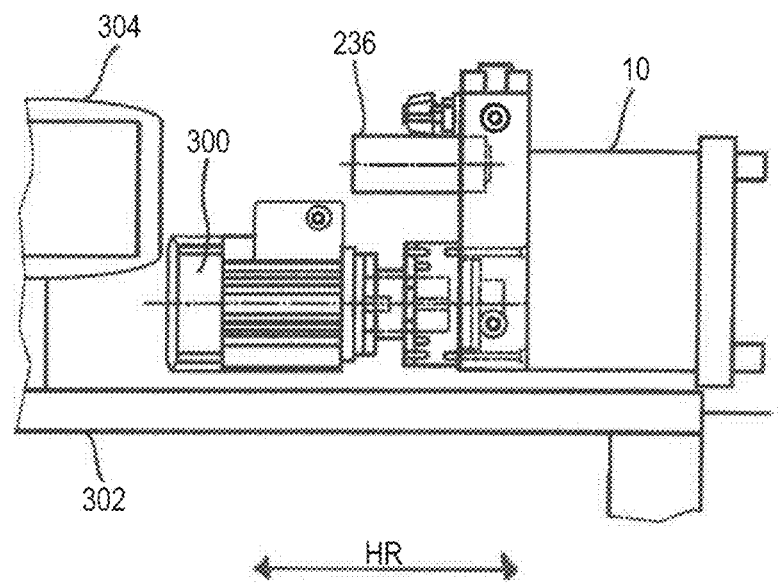

FIGS. 5A and 5B show a work bench 302, on which the filter system 100 can be mounted. The control apparatus 304, described above, can also be arranged, for example, on the work bench 302. As a result of the structural design of the filter system 100, it can be attached to the work bench 302 in both a vertical orientation (see FIG. 5A) and in a horizontal orientation (see FIG. 5B).

In the case of a vertical orientation, the retaining elements 206 can be used to mount the filter system 100 on the work bench 302. In the specific case shown in FIG. 5A, the retaining rods 208 could project beyond the distributor plate 200 in such a way that they also pass through the work bench 302. The lock nuts 210 secure the filter system 100 to the work bench 302.

FIG. 6 shows another embodiment of a filter system 100. In this embodiment the filter system 100 differs from the already described filter systems 100 in that the distributor plate 200 is configured in such a way that the filter area can be expanded by at least two more filter units 10.

The illustrated filter system 100 corresponds to a filter system 100, as shown in FIG. 3, where in this case the distributor plate 200 is expanded to the left, in order to be able to arrange, additionally, at least one filter unit 10 on the extension of the distributor plate 200 on opposite sides. However, it is also possible for at least one filter unit 10 to be arranged only on one side of the extension of the distributor plate 200. In this case the descriptions of FIGS. 1 and 2 also apply here, mutatis mutandis.

In other words, the pump is located centrally on the distributor plate 200; and the distributor plate 200 extends to the left and to the right. At least one filter unit 10 is arranged on each of the two distributor plate halves on opposite sides of the distributor plate 200. Here, the permeate output ports 226 are located on opposite ends of the distributor plate 200, while the retentate output port 240 and the input port 220 are located centrally, preferably at the level of the pump. Explanations for guiding the fluid within the distributor plate 200 with respect to FIGS. 1 and 2 also apply here, mutatis mutandis.

As an alternative, two distributor plates 200 can be coupled to one another, in order to provide the system expansion, shown in FIG. 6.

Therefore, the filter system 100 of the present invention provides a simple and cost effective system that is easy to handle and does not require any hoses. The filter area can also be expanded, as required, in a simple way.

LIST OF REFERENCE NUMERALS AND CHARACTERS 10 filter unit
14 fluid flow
16 filter medium
22 spacer
24 feed flow
26 feed spacer
27 permeate spacer
28 through hole
40 retentate discharge flow
42 permeate discharge flow
100 filter system
200 distributor plate
202 distributor unit
204 end plate
206 retaining element
208 retaining rod
210 lock nut
212 notch
214 first filter unit
216 second filter unit
218 conduit system
220 input port
222 feed line
224 inflow opening
226 permeate output port
228 permeate discharge line
230 permeate discharge opening
232 pump head (active control element)
236 sensor
238 valve (active control element)
240 retentate output port
242 retentate discharge line
244 retentate discharge opening
248 connecting recess
250 valve adjuster
252 feed port
300 pump drive
302 work bench
304 control apparatus
HR horizontal direction
VR vertical direction

What is claimed is:

1. Filter system for biopharmaceutical processes, said filter system comprising:
at least one filter unit; and
a distributor plate, against which the at least one filter unit directly rests and which comprises a distributor unit, which is arranged within the distributor plate and is fluidically connected via a fluid connection to the at least one filter unit;
wherein the distributor unit is configured to:
guide inflow fluid to be filtered from a fluid input port, through more than one inflow fluid opening of a fluid feed line fluidly connected to the fluid input port, to the at least one filter unit, and
receive and discharge the inflow fluid, once filtered, through more than one permeate discharge opening of at least two permeate discharge lines and more than one retentate discharge opening of at least one retentate discharge line, from the at least one filter unit,
wherein the distributor unit comprises at least one active control element, with which inflow fluid flow, which flows through the distributor unit and the at least one filter unit, is controlled in an open loop flow or in a closed loop flow,
wherein the distributor unit is tubeless,
wherein the fluid connection between the at least one filter unit and the distributor plate is tubeless,
wherein the at least one active control element is integrated in the distributor plate between the fluid input port and the inflow fluid openings of the fluid feed line and comprises a pump head configured to connect to a pump drive to pump the inflow fluid through the distributor plate and the at least one filter unit, and
wherein the inflow fluid openings and the permeate discharge openings are located on the distributor plate in one plane arranged along a line in alternating manner, and the retentate discharge openings and the permeate discharge openings are located on the distributor plate in one plane arranged along a line in alternating manner.

2. Filter system as claimed in claim 1, wherein the distributor unit comprises a conduit system, which extends within the distributor plate and is configured to guide the inflow fluid to be filtered and, once filtered, the filtered fluid.

3. Filter system as claimed in claim 1, further comprising a further active control element comprising at least one valve that is configured to control the inflow fluid flow through the distributor plate and the at least one filter unit in the open loop flow or in the closed loop flow.

4. Filter system as claimed in claim 1, wherein the distributor unit comprises at least one sensor configured to measure at least one parameter of the inflow fluid flow within the distributor unit.

5. Filter system as claimed in claim 1, further comprising at least one end plate, which is connected to the distributor plate with at least one retaining element,
wherein the at least one filter unit is arranged between the distributor plate and the end plate and is held on the distributor plate by the end plate.

6. Filter system as claimed in claim 1, wherein the distributor plate is made of plastic.

7. Filter system as claimed in claim 1, wherein the at least one filter unit and/or the distributor plate is configured to be sterilized by gamma irradiation, gassing and/or autoclaving.

8. Filter system as claimed in claim 1, further comprising at least one first filter unit and at least one second filter unit, wherein the at least one first and the at least one second filter unit rest against opposite sides of the distributor plate.

9. Filter system as claimed in claim 1, wherein the at least one filter unit and the distributor plate are adhesively bonded to one another or are injection molded from one piece.

10. Filter system as claimed in claim 3, wherein the at least one valve is integrated in the distributor plate as part of the distributor unit.

11. Filter system as claimed in claim 1, wherein the distributor plate comprises at least two permeate output ports fluidically connected to the permeate discharge openings to discharge filtered fluid from the distributor plate as a permeate.

12. Distributor plate for a filter system for biopharmaceutical processes, said distributor plate comprising a distributor unit, which is arranged within the distributor plate and is configured to fluidically connect via a fluid connection to at least one filter unit, wherein the at least one filter unit rests directly against the distributor plate;
wherein the distributor unit is configured to:
guide inflow fluid to be filtered from a fluid input port, through more than one inflow fluid opening of a fluid feed line fluidically connected to the fluid input port, to the at least one filter unit, and
receive and discharge the inflow fluid, once filtered, through more than one permeate discharge opening of at least two permeate discharge lines and more than one retentate discharge opening of at least one retentate discharge line, from the at least one filter unit,
wherein the distributor unit comprises at least one active control element, with which inflow fluid flow, which flows through the distributor unit and the at least one filter unit, is controlled in an open loop flow or in a closed loop flow,
wherein the distributor unit is tubeless,
wherein the fluid connection between the at least one filter unit and the distributor plate is tubeless,
wherein the at least one active control element is integrated in the distributor plate between the fluid input port and the inflow fluid openings of the fluid feed line and comprises a pump head configured to connect to a pump drive to pump the inflow fluid through the distributor plate and the at least one filter unit, and
wherein the inflow fluid openings and the permeate discharge openings are located on the distributor plate in one plane arranged along a line in alternating manner, and the retentate discharge openings and the permeate discharge openings are located on the distributor plate in one plane arranged along a line in alternating manner.

13. Distributor plate as claimed in claim 12, further comprising a further active control element comprising at least one valve that is configured to control the inflow fluid flow through the distributor plate in the open loop flow or in the closed loop flow.

14. Distributor plate as claimed in claim 13, wherein the at least one valve is integrated in the distributor plate as part of the distributor unit.

15. Filter system as claimed in claim 12, wherein the distributor plate comprises at least two permeate output ports fluidically connected to the permeate discharge openings to discharge filter filtered fluid from the distributor plate as a permeate.

16. Filter system for biopharmaceutical processes, said filter system comprising:
a filter unit comprising at least two layers of a filter medium which are spaced apart from each other by a permeate spacer; and
a distributor plate, against which the filter unit directly rests and which comprises a distributor unit, which is arranged within the distributor plate and is fluidically connected via a fluid connection to the filter unit;
wherein the distributor unit is configured to:
guide inflow fluid to be filtered from a fluid input port, through more than one inflow fluid opening of a fluid feed line, to the filter unit, and
receive and discharge the inflow fluid, once the inflow fluid is filtered, through more than one permeate discharge opening of at least first and second permeate discharge lines and more than one retentate discharge opening of at least one retentate discharge line from the filter unit,
wherein the distributor unit comprises at least one active control element, with which inflow fluid flow, which flows through the distributor unit and the filter unit, is controlled in an open loop flow or in a closed loop flow,
wherein the distributor unit is tubeless,
wherein the fluid connection between the filter unit and the distributor plate is tubeless,
wherein the distributor plate comprises at least first and second permeate output ports to discharge the filtered inflow fluid received from the filter unit from the distributor plate as a permeate,
wherein the first permeate output port is fluidly connected to the permeate discharge openings of the first permeate discharge line, and the second permeate output port is fluidly connected to the permeate discharge openings of the second permeate discharge line,
wherein the inflow fluid openings and the permeate discharge openings are located on the distributor plate in one plane arranged along a line in alternating manner, and the retentate discharge openings and the permeate discharge openings are located on the distributor plate in one plane arranged along a line in alternating manner,
wherein the filter unit fluidly communicates with the permeate discharge openings of the first permeate discharge line as well as the permeate discharge openings of the second permeate discharge line, and
wherein the inflow fluid that passes through the at least two layers of a filter medium is guided by the permeate spacer as a permeate discharge flow simultaneously to the permeate discharge openings of first and second permeate discharge lines to be transported away from the filter unit.

17. Filter system as claimed in claim 16,
wherein the distribution plate has a plurality of sides and the at least first and second permeate output ports are arranged on the same side of the distribution plate, and
wherein the at least first and second permeate output ports arranged on the same side of the distribution plate are positioned with an offset in a vertical direction of the distribution plate.

18. Distributor plate for a filter system for biopharmaceutical processes, said distributor plate comprising a distributor unit, which is arranged within the distributor plate and is configured to fluidically connect via a fluid connection to at least one a filter unit, wherein the filter unit rests directly against the distributor plate and comprises at least two layers of a filter medium which are spaced apart from each other by a permeate spacer, wherein the distributor unit is configured to:
guide inflow fluid to be filtered from a fluid input port, through more than one inflow fluid opening of a fluid feed line, to the filter unit, and
receive and discharge the inflow fluid, once the inflow fluid is filtered, through more than one permeate discharge opening of at least first and second permeate discharge lines and more than one retentate discharge opening of at least one retentate discharge line from the filter unit, wherein the distributor unit comprises at least one active control element, with which inflow fluid flow, which flows through the distributor unit and the filter unit, is controlled in an open loop flow or in a closed loop flow, wherein the distributor unit is tubeless, wherein the fluid connection between the filter unit and the distributor plate is tubeless, wherein the distributor plate comprises at least first and second permeate output ports to discharge the filtered inflow fluid received from the at least one filter unit from the distributor plate as a permeate, wherein the first permeate output port is fluidly connected to the permeate discharge openings of the first permeate discharge line, and the second permeate output port is fluidly connected to the permeate discharge openings of the second permeate discharge line, wherein the inflow fluid openings and the permeate discharge openings are located on the distributor plate in one plane arranged along a line in alternating manner, and the retentate discharge openings and the permeate discharge openings are located on the distributor plate in one plane arranged along a line in alternating manner, wherein the filter unit fluidly communicates with the permeate discharge openings of the first permeate discharge line as well as the permeate discharge openings of the second permeate discharge line, and wherein the inflow fluid that passes through the at least two layers of a filter medium is guided by the permeate spacer as a permeate discharge flow simultaneously to the permeate discharge openings of first and second permeate discharge lines to be transported away from the filter unit.

19. Filter system as claimed in claim 18, wherein the distribution plate has a plurality of sides and the at least first and second permeate output ports are arranged on the same side of the distribution plate, and wherein the at least first and second permeate output ports arranged on the same side of the distribution plate are positioned with an offset in a vertical direction of the distribution plate.

* * * * *